(12) United States Patent
Mendoza

(10) Patent No.: US 12,239,724 B2
(45) Date of Patent: Mar. 4, 2025

(54) LIP COMPOSITION

(71) Applicant: MARY KAY INC., Addison, TX (US)

(72) Inventor: Ricky Mendoza, Addison, TX (US)

(73) Assignee: MARY KAY INC., Addison, TX (US)

( * ) Notice: Subject to any disclaimer, the term of this patent is extended or adjusted under 35 U.S.C. 154(b) by 256 days.

(21) Appl. No.: 17/159,960

(22) Filed: Jan. 27, 2021

(65) Prior Publication Data

US 2021/0228460 A1    Jul. 29, 2021

Related U.S. Application Data

(60) Provisional application No. 62/966,881, filed on Jan. 28, 2020.

(51) Int. Cl.
*A61K 8/42* (2006.01)
*A61K 8/81* (2006.01)
*A61Q 1/06* (2006.01)

(52) U.S. Cl.
CPC .............. *A61K 8/42* (2013.01); *A61K 8/8194* (2013.01); *A61Q 1/06* (2013.01); *A61K 2800/31* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 6,835,373 B2 | 12/2004 | Kolodzik et al. | |
| 7,534,446 B2 | 5/2009 | Rando et al. | |
| 7,611,726 B2 | 11/2009 | Yu | |
| 8,318,141 B2 | 11/2012 | Benavent Bosch et al. | |
| 8,323,628 B2 * | 12/2012 | Atis | A61Q 1/10 424/70.17 |
| 8,679,464 B2 | 3/2014 | Schlossman et al. | |
| 9,433,804 B2 | 9/2016 | Vic et al. | |
| 9,517,196 B2 * | 12/2016 | Smigel | A61K 8/26 |
| 2006/0134035 A1 * | 6/2006 | Zheng | A61Q 1/04 424/70.11 |
| 2007/0154440 A1 * | 7/2007 | Fleissman | A61K 8/898 424/70.122 |
| 2008/0031834 A1 * | 2/2008 | Manelski | A61K 8/898 424/59 |
| 2009/0280076 A1 | 11/2009 | Yoshida et al. | |
| 2011/0182834 A1 | 7/2011 | Do et al. | |
| 2013/0004442 A1 | 1/2013 | Bui et al. | |
| 2015/0132350 A1 | 5/2015 | Arditty et al. | |
| 2015/0139921 A1 * | 5/2015 | Colaco | A61K 8/58 424/59 |
| 2015/0306017 A1 * | 10/2015 | Fanizza | A61K 8/025 424/59 |
| 2016/0008263 A1 * | 1/2016 | Mendoza | A61K 8/31 424/401 |
| 2018/0325800 A1 | 11/2018 | Bernard et al. | |
| 2019/0046438 A1 | 2/2019 | Hnat | |
| 2021/0169751 A1 * | 6/2021 | Brossard | A61K 8/064 |

FOREIGN PATENT DOCUMENTS

| | | | |
|---|---|---|---|
| JP | 2021031427 | * | 8/2019 |
| WO | WO 2009/126854 | | 10/2009 |
| WO | WO 2018/138802 | | 8/2018 |

OTHER PUBLICATIONS

Cosmetics Info Red 7 Lake wayback machine 2015.*
Michalun et al. "Milady Skin Care and Cosmetic Ingredients Dictionary" 2014.*
Database GNPD [Online] Mintel; Aug. 2017 (Aug. 2017), "Lip Icon Lipstick", XP055803113, Database accession No. 5054045.
Database GNPD [Online] Mintel; Jul. 2016 (Jul. 2016), "Scrub Stix Dry Lip Remedy Scrub", XP055803190, Database accession No. 4138537.
International Search Report and Written Opinion issued in Corresponding PCT Application No. PCT/US2021/070082, dated May 21, 2021.

* cited by examiner

*Primary Examiner* — Danah Al-Awadi
(74) *Attorney, Agent, or Firm* — NORTON ROSE FULBRIGHT US LLP

(57) ABSTRACT

Disclosed are lip compositions and methods of their use that include a glutamide derivative and a hydrogenated film forming polymer. The glutamide derivative includes dibutyl lauroyl glutamide and the lip compositions comprise an effective amount of dibutyl lauroyl glutamide to moisturize skin. The lip compositions are further configured to soften skin and provide a high-shine and low tack layer on lips.

11 Claims, No Drawings

LIP COMPOSITION

CROSS REFERENCE TO RELATED APPLICATIONS

The present application claims priority to U.S. provisional patent application 62/966,881, filed Jan. 28, 2020, the disclosure of which is hereby incorporated by reference in its entirety.

BACKGROUND OF THE INVENTION

A. Field of the Invention

The present invention relates generally to lip-based compositions such as lipsticks, lip balms, and lip glosses. A lip-based composition of the present invention is capable of providing high-shine appearance on lips, while also moisturizing the lips to prevent cracked, dried, or chapped lips.

B. Description of Related Art

Previous attempts at lip-based products such as lip sticks have lacked the ability to effectively treat or prevent lip-related conditions (e.g., dried, cracked, chapped lips, etc.) and/or provide high shine appearance of the lips. Attempts to solve these problems have led to formulations that were difficult to spread on the lips, had unpleasant tactile properties (e.g., heavy, oily, tacky, etc.), and had limited beneficial effects for lip-related conditions.

SUMMARY OF THE INVENTION

A solution to at least some of the above-mentioned problems associated with lip-based compositions and/or products has been discovered. The solution resides in a lip-based product such as a lip gloss that is configured to provide high shine appearance on lips and/or high moisturizing efficiency, glide on lips effortlessly, provide healthy looking to the lips, provide light weight feeling on lips, have low tack, have effective amounts of actives to moisturize the lips and treat dry chapped, or cracked lips, and have effective amounts of actives to soften skin. These benefits of the lip-based products are achieved by a unique combination of: (1) a glutamide derivative; (2) a hydrogenated film forming polymer; (3) one or more emollients including, but not limited to, hydrogenated polyisobutene and octyldodecanol. The lip-based products may further include an aesthetically pleasing gellant. The formulation can be transparent, translucent, clear, opaque, water-resistant, and can be used as a base or primer in which additional products (e.g., colored lipsticks or colored lip glosses) are applied on top of the lip formulation of the present invention.

In embodiments of the invention, there is provided a lip composition comprising a glutamide derivative and a hydrogenated film forming polymer. In some aspects, the weight ratio of the glutamide derivative to the hydrogenated film forming polymer can be less than 1:5, preferably 1:16. In some aspects, the glutamide derivative can have a formula of:

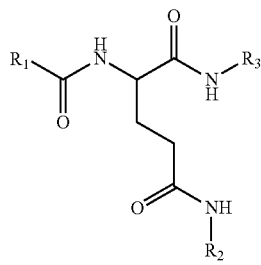

where $R_1$, $R_2$, and $R_3$ can each individually and independently include branched, straight chained, or cyclic alkyl groups having from one to twenty carbon atoms. In some instances, $R_1$ can be selected from branched, straight chain alkyl groups having from two to 16 carbon atoms, and $R_2$ and $R_3$ each individually and independently can be a straight chain alkyl group having from two to six carbon atoms. In some instances, $R_1$ can be a branched or straight chained alkyl group having from three to sixteen carbon atoms, and $R_2$ and $R_3$ are each n-butyl groups. In some instances, $R_1$ can be a straight chain undecyl group, and the glutamide derivative of the formula is dibutyl lauroyl glutamide, which is capable of moisturizing skin. In some instances, the lip composition can include 0.001 to 15 wt. % the glutamide derivative, preferably 0.05 to 5.0 wt. %, more preferably 0.1 to 2.0 wt. % the glutamide derivative and all ranges and values there between including ranges of 0.1 to 0.2 wt. %, 0.2 to 0.4 wt. %, 0.4 to 0.6 wt. %, 0.6 to 0.8 wt. %, 0.8 to 1.0 wt. %, 1.0 to 1.2 wt. %, 1.2 to 1.4 wt. %, 1.4 to 1.6 wt. %, 1.6 to 1.8 wt. %, and 1.8 to 2.0 wt. %. In some aspects, the hydrogenated film forming polymer can include hydrophobic film formers, such as polyolefins, polyvinyls, polyacrylates, polyurethanes, silicones, silicone acrylates, polyamides, polyesters, fluroropolymers, polyethers, polyacetates, polycarbonates, polyimides, rubbers, natural, mineral, synthetic waxes, hydrophobic esters, and/or epoxys. Additionally, the lip composition may comprise hydrophilic and/or water-soluble film formers, such as cellulosics, polysaccharides, and/or polyquaterniums. In some instances, the hydrogenated film forming polymer can include an oil soluble film forming hydrogenated polycyclopentadiene polymer. The glutamide derivative can include dibutyl lauroyl glutamide.

In some aspects, the lip composition can comprise an effective amount of dibutyl lauroyl glutamide to moisturize skin of the lips. In some aspects, the lip composition can be an anhydrous lip product. In some aspects, the lip composition can comprise an emollient. The lip composition may comprise an effective amount of the emollient to soften skin. Non-limiting exemplary emollients can include hydrogenated polyisobutene, and octyldodecanol. The emollient can comprise an oil phase of the lip composition. In some instances, the lip composition may further comprise *Ricinus communis* seed oil, *Simmondsia chinensis* seed oil, and/or *Glycine soja* (soybean) oil. In some instances, the lip composition may include *Aloe barbadensis* leaf extract. In some aspects, the lip composition can include one or more pigments. Non-limiting examples of the pigments can include Blue I, Blue I Lake, Red 40, Red 28 Lake, Red 27 Lake, Red 7 Lake, Red 6 Lake, Yellow 5 Lake, titanium dioxide, aluminum hydroxide, Unipure Red 6, Unipure Red 28, Unipure Red 33, Unipure Yellow OX, Unipure Yellow 5, FD&C Blue I, D&C Blue no. 4, D&C Green no. 5, D&C Orange no. 4, D&C Red no. 17, D&C Red no. 6, D&C Red no. 7, D&C Red no. 30, D&C Red no. 33, D&C Violet no. 2, D&C Yellow no. 10, D&C Yellow no. 11, iron oxides, chromium oxides, tin oxide, ultramarines, mica, and combinations thereof.

In some aspects, the lip composition may include one or more antioxidants. Non-limiting examples of the antioxidants can include tocopherol, tocopheryl acetate, tetrahexyldecyl ascorbate, and combinations thereof. In some aspects, the lip composition can include a material that is configured to increase fluidity of structural properties of lips. The material may be capable of associating with ceramides in stratum corneum of the lips and facilitating inflowing of a hydrating agent into the stratum corneum. Non-limiting examples of the material can include an alkylamide and/or an alkyl ester. The hydrating agent can include glycerin and/or water.

In some instances, the lip composition can comprise 0.001 to 15 wt. % dibutyl lauroyl glutamide, preferably 0.05 to 5.0 wt. %, more preferably 0.1 to 2.0 wt. % dibutyl lauroyl glutamide and all ranges and values there between including ranges of 0.1 to 0.2 wt. %, 0.2 to 0.4 wt. %, 0.4 to 0.6 wt. %, 0.6 to 0.8 wt. %, 0.8 to 1.0 wt. %, 1.0 to 1.2 wt. %, 1.2 to 1.4 wt. %, 1.4 to 1.6 wt. %, 1.6 to 1.8 wt. %, and 1.8 to 2.0 wt. %. In some instances, the lip composition may comprise 0.01 to 30 wt. % hydrogenated polycyclopentadiene and all ranges and values there between including ranges of 0.01 to 0.1 wt. %, 0.1 to 1 wt. %, 1 to 3 wt. %, 3 to 6 wt. %, 6 to 9 wt. %, 9 to 12 wt. %, 12 to 15 wt. %, 15 to 18 wt. %, 18 to 21 wt. %, 21 to 24 wt. %, 24 to 27 wt. %, and 27 to 30 wt. %. In some instances, the lip composition can further comprise 3.9 to 78 wt. % hydrogenated polyisobutene, 1.7 to 34 wt. % octyldodecanol, 0.9 to 80 wt. % *Ricinus communis* (castro) seed oil, 0.01 to 1.0 wt. % tocopheryl acetate, 0.001 to 0.1 wt. % tetrahexyldecyl ascorbate, 0.0005 to 0.05 wt. % tocopherol, 0.0005 to 0.05 wt. % *Glycine soja* (soybean) oil, 0.35 to 13.5 wt. % one or more pigments, and 0.38 to 38 wt. % microcrystalline wax. In some aspects, the lip composition can be configured to provide a low-tack and high shine layer on the lips. The lip composition can include a lip gloss, a lip stick, and/or a lip balm.

In some aspects, the lip composition can include an emulsion of the hydrogenated film forming polymer and the glutamide derivative. The emulsion may further comprise a stabilizer in form of a particle phase. Exemplary stabilizers can include silica, mica, clay, carbon, and/or pigments. The silica can include silica gel, fumed silica, fused silica, precipitated silica, synthesized silica, or any combination thereof. The particle phase can further comprise carbon including activated carbon, charcoal, graphite, and/or black carbon. In some aspects, the particle phase can further include titanium dioxide, clay, other metal oxides, alginate, cellulosics, zeolites, or any combination thereof.

In embodiments of the invention, there is provided a method of improving a condition or appearance of a lip. The method can include applying to the lip an effective amount of a lip composition comprising a glutamide derivative and a hydrogenated film forming polymer. Exemplary conditions of the lip can include dry lips, chapped lips, cracked lips, and combinations thereof. In some aspects, by applying the lip composition, the lip may be treated to increase a moisture level thereof. In some aspects, by applying the lip composition, the lip may be treated to soften skin thereof. In some instances, the lip moisture level can be increased within about 15 minutes of applying the lip composition. In some aspects, the lip composition may be applied to provide high-shine appearance to the lips. In some aspects, the lip composition can be applied to provide a low-tack layer on the lips. The lip composition may remain on the lips for at least 1 minute.

In some aspects, the lip composition can include a material that is configured to increase fluidity of structural properties of lips. In some instances, the lip composition can be applied to associate with ceramides in stratum corneum of lips and facilitate inflowing of a hydrating agent into the stratum corneum. The hydrating agent can include glycerin and/or water. In some aspects, the weight ratio of the glutamide derivative to the hydrogenated film forming polymer can be less than 1:5, preferably 1:16. In some aspects, the hydrogenated film forming polymer can include hydrophobic film formers, such as polyolefins, polyvinyls, polyacrylates, polyurethanes, silicones, silicone acrylates, polyamides, polyesters, fluropolymers, polyethers, polyacetates, polycarbonates, polyimides, rubbers, natural, mineral, synthetic waxes, hydrophobic esters, epoxys, or any combination thereof. The lip composition may comprise hydrophilic and/or water-soluble film formers, such as cellulosics, polysaccharides, and/or polyquaterniums. In some instances, the hydrogenated film forming polymer can include an oil soluble film forming hydrogenated polycyclopentadiene polymer. In some aspects, the glutamide derivative can have a formula of:

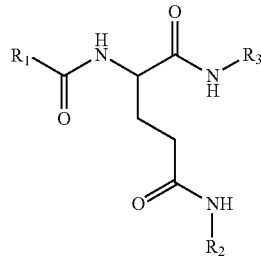

where $R_1$, $R_2$, and $R_3$ can each individually and independently include branched, straight chained, or cyclic alkyl groups having from one to twenty carbon atoms. In some instances, $R_1$ can be selected from branched, straight chain alkyl groups having from two to 16 carbon atoms, and $R_2$ and $R_3$ each individually and independently can be a straight chain alkyl group having from two to six carbon atoms. In some instances, $R_1$ can be a branched or straight chained alkyl group having from three to sixteen carbon atoms, and $R_2$ and $R_3$ are each n-butyl groups. In some instances, $R_1$ can be a straight chain undecyl group, and the glutamide derivative of the formula is dibutyl lauroyl glutamide, which is capable of moisturizing skin. In some aspects, the applied lip composition can include an effective amount of dibutyl lauroyl glutamide to moisturize skin. The lip composition can include an emollient. Exemplary emollients can include hydrogenated polyisobutene, and/or octyldodecanol. In some aspects, the applied lip composition can include an effective amount of the emollient to soften skin. The emollient can comprise an oil phase of the lip composition. In some aspects, the applied lip composition can further include *Ricinus communis* seed oil, *Simmondsia chinensis* seed oil, and/or *Glycine soja* (soybean) oil. The applied lip composition can include one or more pigments. In some instances, the applied lip composition comprises 0.12 to 12 wt. % dibutyl lauroyl glutamide, and 0.01 to 30 wt. % hydrogenated polycyclopentadiene. In some instances, the applied lip composition can comprise 3.9 to 78 wt. % hydrogenated polyisobutene, 1.7 to 34 wt. % octyldodecanol, 0.9 to 80 wt. % *Ricinus communis* (castro) seed oil, 0.01 to 1.0 wt. % tocopheryl acetate, 0.001 to 0.1 wt. % tetrahexyldecyl ascorbate, 0.0005 to 0.05 wt. % tocopherol, 0.0005 to 0.05 wt. % *Glycine soja* (soybean) oil, 0.35 to 13.5 wt. % one or more pigments, and 0.38 to 38 wt. % microcrystalline wax.

The applied lip composition can include one or more pigments. Non-limiting examples of pigments can include Blue I, Blue I Lake, Red 40, Red 28 Lake, Red 27 Lake, Red 7 Lake, Red 6 Lake, Yellow 5 Lake, titanium dioxide, aluminum hydroxide, Unipure Red 6, Unipure Red 28, Unipure Red 33, Unipure Yellow OX, Unipure Yellow 5, FD&C Blue I, D&C Blue no. 4, D&C Green no. 5, D&C Orange no. 4, D&C Red no. 17, D&C Red no. 6, D&C Red no. 7, D&C Red no. 30, D&C Red no. 33, D&C Violet no. 2, D&C Yellow no. 10, D&C Yellow no. 11, iron oxides, chromium oxides, tin oxide, ultramarines, mica, and combinations thereof. In some instances, the applied lip composition can comprise 0.01 to 15 wt. % dibutyl lauroyl glutamide, and 0.01 to 30 wt. % hydrogenated polycyclopentadiene. In some instances, the applied lip composition can further comprise 3.9 to 78 wt. % hydrogenated polyisobutene, 1.7 to 34 wt. % octyldodecanol, 0.9 to 80 wt. % *Ricinus communis* (castro) seed oil, 0.01 to 1.0 wt. % tocopheryl acetate, 0.001 to 0.1 wt. % tetrahexyldecyl ascorbate, 0.0005 to 0.05 wt. % tocopherol, 0.0005 to 0.05 wt. % *Glycine soja* (soybean) oil, 0.35 to 13.5 wt. % one or more pigments, and 0.38 to 38 wt. % microcrystalline wax.

In some aspects, the lip composition can include an emulsion of the hydrogenated film forming polymer and the glutamide derivative. The emulsion may comprise a stabilizer in form of a particle phase. Exemplary stabilizer can include silica, mica, clay, carbon, and/or pigments. The silica can include silica gel, fumed silica, fused silica, precipitated silica, and synthesized silica. The particle phase can comprise carbon including activated carbon, charcoal, graphite, or black carbon. In some aspects, the particle phase can further include titanium dioxide, clay, other metal oxides, alginate, cellulosic, zeolites, or any combination thereof.

In some aspects, the lip compositions may include sunscreen reagent. The compositions can be sunscreen lotions, sprays, or creams. Non-limiting examples for the sun screen reagent may include but are not limited to octinoxate, zinc oxide, ethylhexyl salicylate, ensulizole, homosalate, avobenzone, octocrylene, oxybenzone, or combinations thereof. In some instances, the lip composition may have a sun protection factor (SPF) in a range of 2 to 100 and all ranges and values there between such as SPF 2, SPF 15, SPF 25, SPF 30, SPF 35, SPF 40, SPF 50, SPF 60, SPF70, SPF75, SPF 80, SPF90 and SPF 100.

The compositions of the present invention can also include any one of, any combination of, or all of the following additional ingredients: a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference. The topical composition can be formulated as a mask, lotion, cream, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The topical composition can be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include methylparaben, propylparaben, or a mixture of methylparaben and propylparaben. In some embodiments, the composition is paraben-free.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin including lips for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

In one embodiment, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a gel, a wash, a foundation, a night cream, a lipstick, a cleanser, a toner, a sunscreen, a mask, an anti-aging product, a deodorant, an antiperspirant, a perfume, a cologne, etc.

Also disclosed is a method of tightening or toning skin comprising topically applying to skin in need thereof a composition comprising any one of the compositions of the present invention, wherein topical application of said composition to skin tightens or tones said skin. The compositions disclosed above and throughout this specification can be used.

An additional embodiment includes an injectably acceptable solution comprising any one of the aforementioned combination of ingredients. An injectably acceptable solution includes a solution that can be safely injected into a human or animal.

It is also contemplated that compositions of the present invention can be included into food-based products (e.g., beverages, fortified water, energy drinks, nutritional drinks, solid foods, vitamins, supplements, etc.) and pharmaceutical products (e.g., pills, injectable solutions, drugs, etc.). "Supplements" can include vitamins, minerals, herbs or other botanicals, amino acids, enzymes and metabolites. Such supplements are suitable for oral consumption and can be administered orally.

It is contemplated that any embodiment discussed in this specification can be implemented with respect to any method or composition of the invention, and vice versa. Furthermore, compositions of the invention can be used to achieve methods of the invention.

In the context of the present invention, at least the following 43 aspects are described. Aspect 1 includes a lip composition. The lip composition comprises a glutamide derivative and a hydrogenated film forming polymer. Aspect 2 depends on aspect 1, wherein the weight ratio of the glutamide derivative to the hydrogenated film forming polymer is less than 1:5. Aspect 3 depends on any of aspects 1 and 2, wherein the hydrogenated film forming polymer comprises a hydrophobic film former including polyolefins, polyvinyls, polyacrylates, polyurethanes, silicones, silicone acrylates, polyamides, polyesters, fluoropolymers, polyethers, polyacetates, polycarbonates, polyimides, rubbers, one or more natural minerals, synthetic waxes, hydrophobic esters, epoxys, or any combination thereof. Aspect 4 depends on any of aspects 1 to 3, wherein the hydrogenated film forming polymer includes a hydrophilic and/or water-soluble film former comprising cellulosics, polysaccharides, and/or polyquaterniums. Aspect 5 depends on any of aspects 1 to 4, wherein the hydrogenated film forming polymer includes an oil soluble film forming hydrogenated polycyclopentadiene polymer. Aspect 6 depends on any of aspects 1 to 6, wherein the glutamide derivative has the following structure:

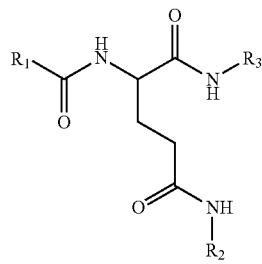

wherein R1, R2, and R3 can each individually and independently include branched, straight chained, or cyclic alkyl groups having from one to twenty carbon atoms. Aspect 7 depends on aspect 6, wherein the glutamide derivative includes dibutyl lauroyl lauroyl glutamide, and the lip composition comprises an effective amount of dibutyl lauroyl glutamide to moisturize skin. Aspect 8 depends on any of aspects 1 to 7, wherein the lip composition is an anhydrous lip product. Aspects 9 depends on any of aspects 1 to 8, wherein the lip composition further comprises an emollient including hydrogenated polyisobutene, and/or octyldodecanol. Aspect 10 depends on aspect 9, wherein the lip composition comprises an effective amount of the emollient to soften skin. Aspect 11 depends on any of aspects 1 to 10, wherein the lip composition further comprises one or more pigments. Aspect 12 depends on any of aspects 1 to 11, wherein the lip composition further comprises a stabilizer in form of a particle phase including silica, mica, clay, carbon, pigments, or any combination thereof. Aspect 13 depends on any of aspects 1 to 12, wherein the lip composition further comprises one or more antioxidants including tocopherol, tocopheryl acetate, tetrahexyldecyl ascorbate, or any combination thereof. Aspect 14 depends on any of aspects 1 to 13, wherein the lip composition further comprises a material configured to increase fluidity of structural properties of lips. Aspect 15 depends on aspect 14, wherein the material includes an alkylamide and/or an alkyl ester. Aspect 16 depends on any of aspects 14 and 15, wherein the material is capable of associating with ceramides in stratum corneum of lips and facilitating inflowing of a hydrating agent into the stratum corneum. Aspect 17 depends on aspect 16, wherein the hydrating agent includes glycerin and/or water. Aspect 18 depends on any of aspects 1 to 17, wherein lip composition comprises 0.01 to 15 wt. % dibutyl lauroyl glutamide, and 0.01 to 30 wt. % hydrogenated polycyclopentadiene. Aspect 19 depends on any of aspects 1 to 18, wherein the lip composition comprises 3.9 to 78 wt. % hydrogenated polyisobutene, 1.7 to 34 wt. % octyldodecanol, 0.9 to 80 wt. % *Ricinus communis* (castro) seed oil, 0.01 to 1.0 wt. % tocopheryl acetate, 0.001 to 0.1 wt. % tetrahexyldecyl ascorbate, 0.0005 to 0.05 wt. % tocopherol, 0.0005 to 0.05 wt. % *Glycine soja* (soybean) oil, 0.35 to 13.5 wt. % one or more pigments, and comprises 0.38 to 38 wt. % microcrystalline wax. Aspect 20 depends on any of aspects 1 to 19, wherein the lip composition is configured to provide a low-tack and high shine layer on the lips. Aspect 21 depends on any of aspects 1 to 20, wherein the lip composition comprises a lip gloss, a lip stick, and/or a lip balm. Aspect 22 includes a method of improving a conditions or appearance of a lip. The method comprises applying to the lip an effective amount of a lip composition comprising a glutamide derivative and a hydrogenated film forming polymer. Aspect 23 depends on aspect 22, wherein the lip is treated to reduce condition comprising dry lips, chapped lips, cracked lips, or any combination thereof. Aspect 24 depends on any of aspects 22 and 23, wherein the lip is treated to increase moisture level thereof. Aspect 25 depends on any of aspects 22 to 24, wherein the lip is treated to soften skin thereof. Aspect 26 depends on any of aspects 22 to 25, wherein the lip moisture level is increased within about 15 minutes of applying the lip composition. Aspect 27 depends on any of aspects 22 to 26, wherein the lip composition is applied to provide high-shine appearance to the lips. Aspect 28 depends on any of aspects 22 to 27, wherein the lip composition is applied to provide a low-tack layer on the lips. Aspect 29 depends on any of aspects 22 to 28, wherein the lip composition remains on the lips for at least 1 minute. Aspect 30 depends on any of aspects 22 to 29, wherein the lip composition comprising a material configured to increase fluidity of structural properties of lips. Aspect 31 depends on any of aspects 22 to 30, wherein the lip composition is applied to associate with ceramides in stratum corneum of lips and facilitate inflowing of a hydrating agent into the stratum corneum. Aspect 32 depends on aspect 31, wherein the hydrating agent includes glycerin and/or water. Aspect 33 depends on any of aspects 22 to 32, wherein, in the lip composition, the weight ratio of the glutamide derivative to the hydrogenated film forming polymer is less than 1:5. Aspect 34 depends on any of aspects 22 to 33, wherein the hydrogenated film forming polymer includes an oil soluble film forming hydrogenated polycyclopentadiene polymer. Aspect 35 depends on any of aspects 22 to 34, wherein the glutamide derivative includes dibutyl lauroyl glutamide. Aspect 36 depends on aspect 35, wherein the lip composition comprises an effective amount of dibutyl lauroyl glutamide to moisturize skin. Aspect 37 depends on any of aspects 22 to 36, wherein the lip composition further comprises *Ricinus communis* seed oil, *Simmondsia chinensis* seed oil, and/or *Glycine soja* (soybean) oil. Aspect 38 depends on any of aspects 22 to 37, wherein the lip composition further comprises an emollient including hydrogenated polyisobutene, and/or octyldodecanol. Aspect 39 depends on any of aspects 22 to 38, wherein the lip composition comprises an effective amount of the emollient to soften skin. Aspect 40 depends on any of aspects 38 and 39, wherein the emollient comprises an oil phase of the lip composition. Aspect 41 depends on any of aspects 22 to 40, wherein the lip composition further comprises one or more pigments. Aspect 42 depends on any of aspects 22 to 41, wherein the lip composition comprises 0.01 to 15 wt. % dibutyl lauroyl glutamide, and 0.01 to 30 wt. % hydrogenated polycyclopentadiene. Aspect 43 depends on any of aspects 22 to 42, wherein the lip composition comprises 3.9 to 78 wt. % hydrogenated polyisobutene, 1.7 to 34 wt. % octyldodecanol, 0.9 to 80 wt. % *Ricinus communis* (castro) seed oil, 0.01 to 1.0 wt. % tocopheryl acetate, 0.001 to 0.1 wt. % tetrahexyldecyl ascorbate, 0.0005 to 0.05 wt. % tocopherol, 0.0005 to 0.05 wt. % *Glycine soja* (soybean) oil, 0.35 to 13.5 wt. % one or more pigments, and 0.38 to 38 wt. % microcrystalline wax.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "fluidity of the structural properties of the lips," as that term is used in the specification and/or claims refers to fluid lipid nature of stratum corneum of lips up unto vermilion border. The term "increase fluidity of the structural properties of the lips" can be used to describe an effect of film former that dries down and holds a lip product to the fluid lipid of lips.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods disclosed in this specification includes the compositions' abilities to provide high-shine appearance on lips, while also moisturize the lips to prevent cracked, dried, or chapped lips.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

As noted above, the present invention provides a solution to the problems associated with lip-based composition. The solution is premised on combinations of ingredients and other compounds to soften the skin of lips, moisturize lips, provide high-shine appearance to lips, and provide a light weight and low tack layer on lips. The combinations of ingredients and other compounds can include a glutamide derivative and a hydrogenated film forming polymer.

These and other non-limiting aspects of the present invention are described in the following sections A. Active Ingredients The present invention is premised on a determination that a combination of active ingredients—a glutamide derivative including dibutyle lauroyl glutamide and a film forming polymer including hydrogenated polycyclopentadiene polymer—can be used to improve lips' visual appearance, increase the moisture level of lips, and provide a high shine, low tack, and light weight layer on the lips.

The combinations of ingredients can be used in different products to treat various skin conditions for lips and improve the appearance of lips. By way of non-limiting examples, the combinations of ingredients can be formulated in a lip gloss, a lip balm, or a lipstick.

A glutamide derivative can have a formula of:

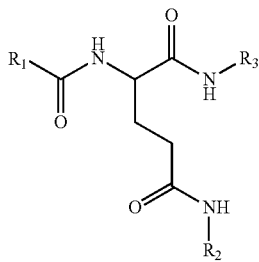

where $R_1$, $R_2$, and $R_3$ can each individually and independently include branched, straight chained, or cyclic alkyl groups having from one to twenty carbon atoms. In some instances, $R_1$ can be selected from branched, straight chain alkyl groups having from two to 16 carbon atoms, and $R_2$ and $R_3$ each individually and independently can be a straight chained alkyl group having from two to six carbon atoms. In some instances, $R_1$ can be a branched or straight chained alkyl group having from three to 16 carbon atoms, and $R_2$ and $R_3$ are each n-butyl groups. In some instances, $R_1$ can be a straight chained undecyl group, and the glutamide derivative of the formula is dibutyl lauroyl glutamide, which is capable of moisturizing skin.

A hydrogenated film forming polymer can include a hydrogenated polycyclopentadiene polymer. In some instances, the hydrogenated polycylopentadiene polymer can be supplied by Kobo Products, Inc. under the trade name of Koboguard® 5400.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3% 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers and/or reflectors (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., *Aloe* extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, saccharide isomerate, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinfera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MWA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, Macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, Eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostastics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Lip Gloss Formulation

Formulations having combinations of ingredients disclosed herein were prepared as lip compositions. The formulations in Tables 1 to 3 were prepared as lip glosses.

TABLE 1*

| Ingredient | Amount (% w/w) |
| --- | --- |
| Hydrogenated polycyclopentadiene | 10.0 |
| Dibutyl lauroyl glutamide | 1.20 |
| Hydrogenated polyisobutene | 38.91 |
| Octyldodecanol | 17.0 |
| Carprylic/Capric Triglyceride | 10.0 |
| Ricinus communis (castor) seed oil | 8.50 |
| Microcrystalline wax/Cire Microcristalline | 3.75 |
| C10-30 Chlesterol/Lanosterol esters | 3.50 |
| Isonoyl isononanoate | 2.92 |
| Titanium dioxide | 0.755 |
| Red 7 lake (pgment) | 0.692 |
| Ethylene/Propylene/Styrene Copolymer | 0.490 |
| Flavor/Aroma | 0.200 |
| Isopropyl myristate | 0.158 |
| Stearalkonium hectorite | 0.122 |
| Tocopheryl acetate | 0.100 |
| Butylene/Ethylene/Copolymer | 0.070 |
| Pentaerythrityl tetra-di-t-butyl Hydroxyhydrocinnamate | 0.050 |
| Isopropyl titanium triisostearate | 0.030 |
| Propylene carbonate | 0.022 |
| Tetrahexyldecyl ascorbate | 0.010 |
| Tocopherol | 0.005 |
| Glycine soja (soybean) oil | 0.005 |
| Polyhydroxystearic acid | 0.004 |
| BHT | 0.004 |
| Synthetic fluorphlogopite | 0.002 |
| Alumina | 0.001 |
| Aluminum calcium sodium silicate | 0.001 |
| Aluminum hydroxide | 0.001 |
| Calcium aluminum borosilicate | 0.001 |
| Calcium sodium borosilicate | 0.001 |
| MICA | 0.001 |
| Tin oxide | 0.00002 |
| Excipients** | q.s. |
| TOTAL | 100 |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition.

TABLE 2*

| Ingredient | Amount (% w/w) |
| --- | --- |
| Hydrogenated polycyclopentadiene | 5.0 |
| Dibutyl lauroyl glutamide | 1.0 |
| Hydrogenated polyisobutene | 29.39 |
| Octyldodecanol | 17.0 |
| Silica and *Ricinus communis* (castor) seed oil (CO15M5) | 10.0 |
| Mica and Isopropyl Titanium Triisostearate | 0.01 |
| Pigment 1 | 0.07 |
| *Simmondsia chinensis* (Jojoba) see oil | 7.00 |
| Vanilla flavor | 0.20 |
| Tetrahexyldecyl ascorbate | 0.01 |
| Tocopheryl acetate | 0.10 |
| Pigment 2 | 2.25 |
| Pigment 3 | 1.00 |
| Microcrystalline wax | 3.25 |
| Pentaerythrityl tetra-di-t-butyl hydroxyhydrocinnamate | 0.05 |
| Isonoyl isononanoate | 2.0 |
| Pigment 4 | 3.15 |
| Parleam gel | 7.0 |
| C10-30 Cholesterol/Lanosterol ester | 3.50 |
| Pentaerythrityl tetraisostearate | 8.0 |
| Pearl blend | 0.01 |
| Titanium dioxide | 0.01 |
| Tocopherol | 0.01 |
| Excipients** | q.s. |
| TOTAL | 100 |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition.

TABLE 3

| Ingredient | Amount (% w/w) |
| --- | --- |
| Hydrogenated polycyclopentadiene | 20.0 |
| Dibutyl lauroyl glutamide | 1.20 |
| Hydrogenated polyisobutene | 29.39 |
| Octyldodecanol | 17.0 |
| Silica and *Ricinus communis* (castor) seed oil (CO15M5) | 10.0 |
| Mica and Isopropyl Titanium Triisostearate | 0.01 |
| Pigment 1 | 0.07 |
| Vanilla flavor | 0.20 |
| Tetrahexyldecyl ascorbate | 0.01 |
| Tocopheryl acetate | 0.10 |
| Pigment 2 | 2.25 |
| Pigment 3 | 1.00 |
| Microcrystalline wax | 3.75 |
| Pentaerythrityl tetra-di-t-butyl hydroxyhydrocinnamate | 0.05 |
| Isonoyl isononanoate | 2.00 |
| Pigment 4 | 1.35 |
| Parleam gel | 7.0 |
| C10-30 Cholesterol/Lanosterol ester | 3.50 |
| Pearl blend | 0.01 |
| Titanium dioxide | 0.01 |
| Tocopherol | 0.01 |
| Excipients** | q.s. |
| TOTAL | 100 |

*Formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition.
**Excipients can be added, for example, to modify the rheological properties of the composition.

Example 2

(Consumer Study for Lip Composition)

Consumer study was conducted to test a lip composition that include the active ingredients and other ingredients as described above. The lip composition was formulated as a lip gloss contained in an applicator. A hundred subjects in the age range of 18 to 65 years old participated the study. After one day immediate use, 96% subjects confirmed that their lips feel moisturized instantly, and 93% subjects confirmed that their lips instantly look hydrated.

TABLE 4

Consumer study results after one day immediate use

| Total Subjects n = 100 | Percentage of subjects with positive results |
| --- | --- |
| Lips Instantly Feel Moisturized | 96% |
| Lips Instantly Look Hydrated | 93% |

After seven days of use, 98% subjects confirmed that the lip composition glides on lips effortlessly. 93% subjects confirmed that the lip composition leaves lips looking shiny. About 91% subjects confirmed that the lip composition leaves lips looking healthy. About 91% subjects confirmed that the lip composition provides an elegant shine. About 90% subjects confirmed that the lip composition leaves lips feeling silky-smooth, and about 84% subjects confirmed that the applicator dispenses the right amount of lip gloss with every swipe. About 83% subjects confirmed that the lip gloss does not feel tacky, and about 79% subjects confirmed that the lip gloss feels lightweight and about 76% subjects feels the lip gloss is not sticky.

TABLE 5

Consumer study results after seven-day use

| Attribution | Agree % |
| --- | --- |
| Glides on effortlessly | 98% |
| Leaves lips looking shiny | 93% |
| Leaves lips looking healthy | 91% |
| Provides an elegant shine | 91% |
| Leaves lips feeling silky-smooth | 90% |
| Applicator dispenses the right amount with every swipe | 84% |
| Does not feel tacky | 83% |
| Feels lightweight | 79% |
| Does not feel sticky | 76% |

The 100 subjects further rated the lip gloss on a scale of 1 to 9 with 1 meaning dislike extremely and 9 means like extremely. The mean score for this lip gloss was 7.7. With about 24% subjects like it extremely (score 9), about 41% subjects like the lip gloss very much (score 8), and about 25% subjects like the lip gloss moderately (score 7). About 6% subjects like the lip gloss slightly (score 6). Less than 4% subjects dislike the lip gloss product (score below 4).

Example 3

(Assays that can be Used to Test Compositions)

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm and cellular viability is quantified.

Collagen Stimulation Assay: Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. For generation of samples and controls, subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin Stimulation Assay: Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ. Laminin secretion can be monitored by quantifying laminin in cell supernatants of cultured human fibroblasts treated for 3 days with culture medium with or without 1.0% final concentration of the test ingredient(s). Following incubation, laminin content can be measured using immunofluorescent antibodies directed against laminin in an enzyme linked immunosorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Nitric Oxide Synthase Activity Assay: Nitric oxide synthases (NOS) are a family of enzymes catalyzing the production of nitric oxide (NO) from L-arginine. NOS is an important mediator of vasodilation in blood vessels. This bioassay was used to analyze the effect of saccharide isomerate extract and *Myrothamnus flabellifolia* extract on the activity of NOS. The bioassay is performed in the presence or absence of the test compound, test extract, or positive control during production of NO by NOS. To measure the activity of NOS under, the NO product is allowed to oxidize to nitrite and nitrate and then the nitrate is reduced to nitrite and measured using an improved Griess method.

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Michigan USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®+ by metmyoglobin. The capacity of the antioxidants in the sample to prevent ABTS oxidation can be compared with that Trolox, a water-soluble tocopherol analogue, and can be quantified as a molar Trolox equivalent.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water-soluble vitamin E analog, serves as positive control inhibition fluorescein decay in a dose dependent manner.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase 3 and 9 Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1cm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: EnzChek® Elastase Assay (Kit #E-12056) from Molecular Probes (Eugene, Oregon USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin—Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® Simon™ western blotting protocol. For each sample, normal human epidermal keratinocytes (NHEK) are grown in EPI-200—Mattek Epilife® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® Simon™ western blottingbioassay assay employs quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin—Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® Simon™ western blotting protocol. For the samples, adult human epidermal keratinocytes (HEKa) from Life Technologies (C-005-5C) can be grown at 37° C. and 5% CO2 for 24 hours in Epilife growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® Simon™ western blottingbioassay assay employs quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability—Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid—Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity—Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of improving a condition or appearance of a lip comprising applying to the lip an effective amount of a lip composition comprising:
   0.01 to 15 wt. % of a glutamide derivative comprising dibutyl lauroyl glutamide,
   0.01 to 30 wt. % of a hydrogenated film forming polymer comprising a hydrogenated polycyclopentadiene,
   30 to 50 wt. % of hydrogenated polyisobutene,
   15 to 25 wt. % of octyldodecanol,
   0.004 to 10 wt. % of one or more seed oil comprising *Ricinus communis* seed oil and/or *Glycine soja* (soybean) oil and/or a mixture thereof,
   0.01 to 30 wt. % of caprylic/capric triglyceride,
   0.01 to 4 wt. % of C10-30 cholesterol,
   0.01 to 5 wt. % of isononyl isononanoate, and
   0.01 to 5 wt. % of silica,
wherein the lip composition is a lip gloss and is applied to provide a shiny appearance to the lips after application to the lips.

2. The method of claim 1, wherein the lip is treated to reduce condition comprising dry lips, chapped lips, cracked lips, or any combination thereof.

3. The method of claim 1, wherein the lip is treated to increase moisture level thereof and/or soften skin thereof.

4. The method of claim 1, wherein the lip composition is applied to provide a low-tack layer on the lips.

5. The method of claim 1, wherein the lip composition is applied to associate with ceramides in stratum corneum of lips and facilitate inflowing of a hydrating agent into the stratum corneum.

6. The method of claim 1, wherein, in the lip composition, the weight ratio of the glutamide derivative to the hydrogenated film forming polymer is less than 1:5.

7. The method of claim 1, wherein the hydrogenated polycyclopentadiene is oil soluble.

8. The method of claim 1, wherein the lip composition comprises 0.1 to 2 wt. % dibutyl lauroyl glutamide.

9. The method of claim 1, wherein the lip composition further comprises microcrystalline wax.

10. The method of claim 1, wherein the lip composition further comprises one or more of tocopherol, tocopheryl acetate, and tetrahexyldecyl ascorbate.

11. The method of claim 1, wherein the lip composition further comprises titanium dioxide, Red 7 lake, ethylene/propylene/styrene copolymer, isopropyl myristate, and stearalkonium hectorite.

* * * * *